United States Patent [19]

Linhardt et al.

[11] Patent Number: 4,847,338
[45] Date of Patent: Jul. 11, 1989

[54] LOW MOLECULAR WEIGHT HEPARIN FRAGMENTS AS INHIBITORS OF COMPLEMENT ACTIVATION

[75] Inventors: Robert J. Linhardt; Zohar M. Merchant; John M. Weiler, all of Iowa City, Iowa; Murali Sharath, Virginia Beach, Va.

[73] Assignee: University of Iowa Research Foundation, Iowa City, Iowa

[21] Appl. No.: 63,170

[22] Filed: Jun. 17, 1987

Related U.S. Application Data

[63] Continuation of Ser. No. 717,213, Mar. 28, 1985, abandoned.

[51] Int. Cl.$^4$ .................... C07H 13/12; A61K 31/725
[52] U.S. Cl. .................................................. 536/54
[58] Field of Search ........................... 514/56; 536/54

[56] References Cited

U.S. PATENT DOCUMENTS 3,636,282  1/1972  Klein ..................................... 514/56
3,766,167 10/1973  Lasker et al. ......................... 536/54
4,098,995  7/1978  Gopalannair et al. ................ 536/54
4,240,163 12/1980  Galin ..................................... 427/2
4,607,025  8/1986  Petiton et al. ......................... 514/53

FOREIGN PATENT DOCUMENTS 0134502  3/1985  European Pat. Off. .
0163582 12/1985  European Pat. Off. .
1015894  1/1986  Japan .

OTHER PUBLICATIONS

Chem Abst, 103:4756w, 1985.
Chem Abst. 103:326f, 1985.

Primary Examiner—John W. Rollins
Attorney, Agent, or Firm—Seed and Berry

[57] ABSTRACT

There is disclosed a tetrasaccharide, a hexasaccharide, on octasaccharide and a decasaccharide all capable of inhibiting complement activation and having less tha 33% of undigested native heparin's anticoagulation activity.

8 Claims, 6 Drawing Sheets

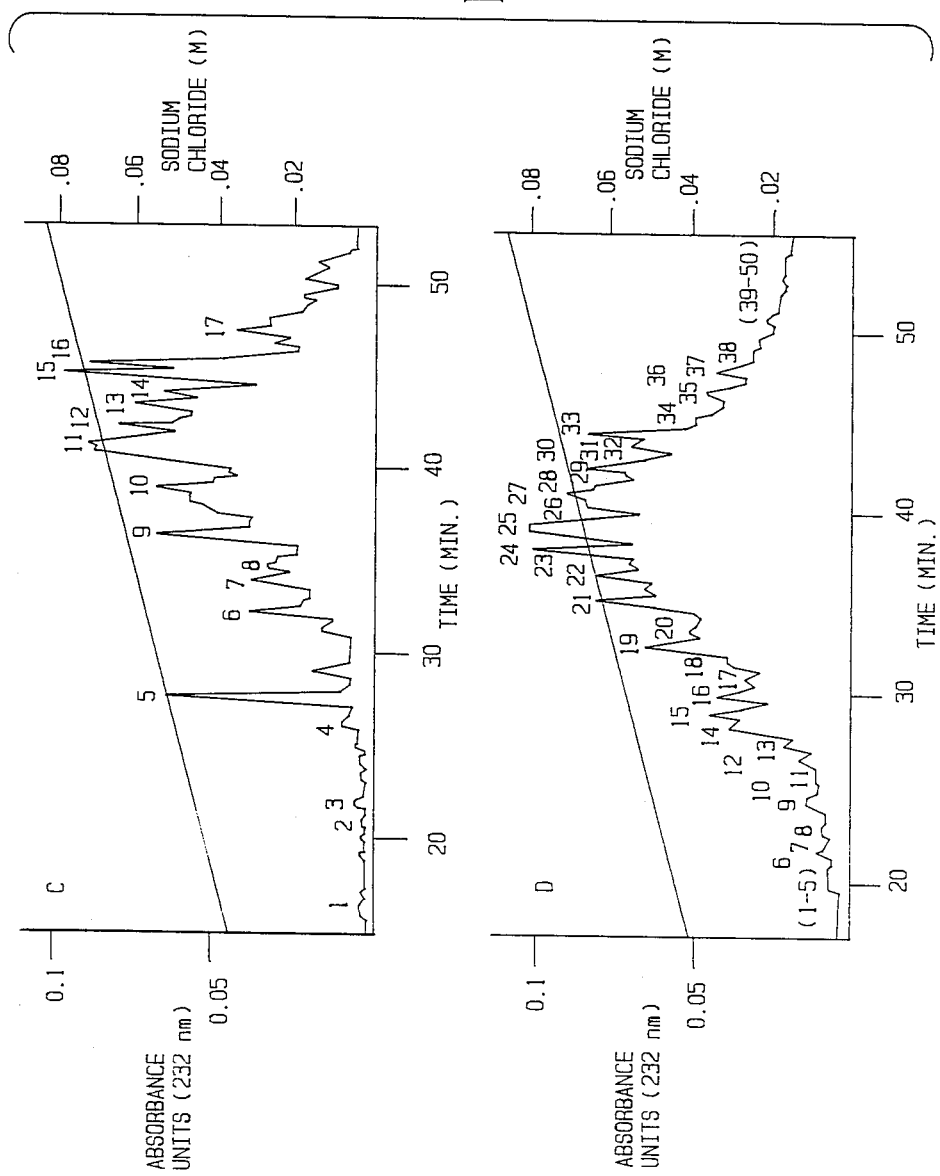

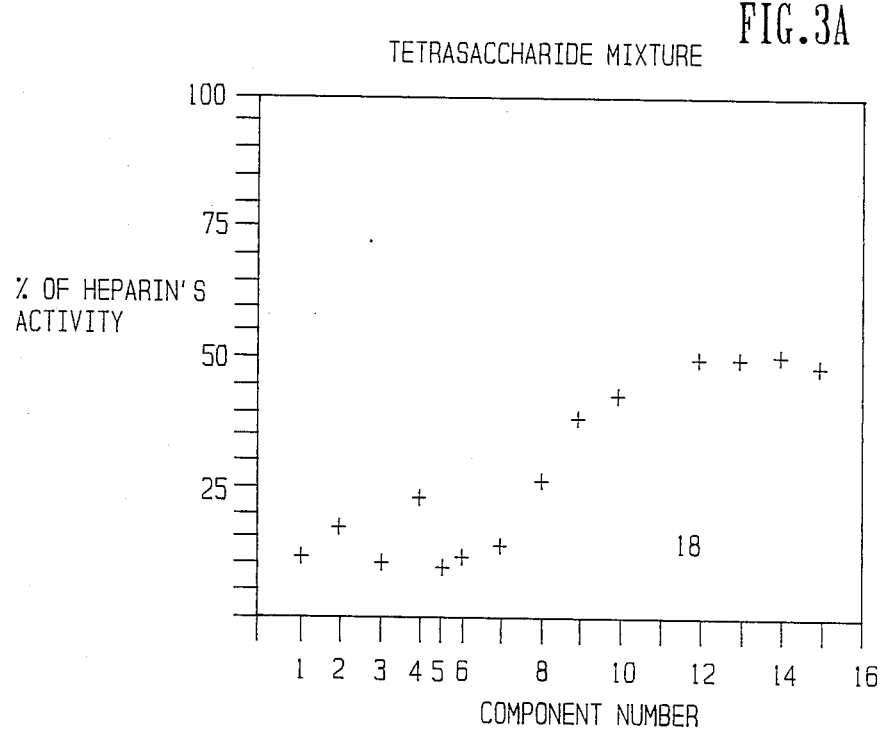
FIG. 3A Tetrasaccharide Mixture
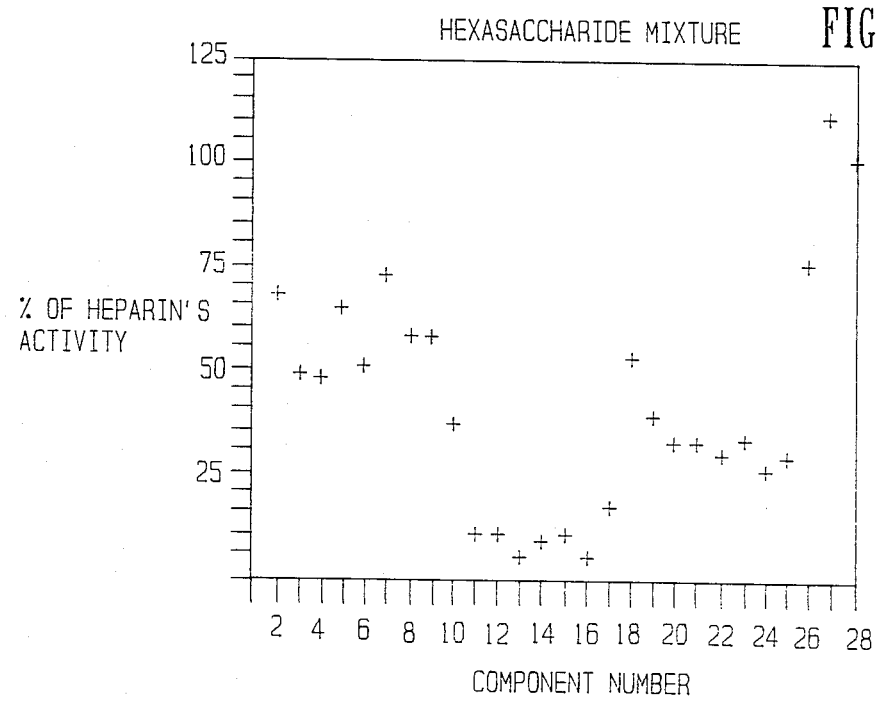
FIG. 3B Hexasaccharide Mixture

LOW MOLECULAR WEIGHT HEPARIN FRAGMENTS AS INHIBITORS OF COMPLEMENT ACTIVATION

This application is a continuation of U.S. patent application Ser. No. 717,213, filed Mar. 28, 1985, now abandoned.

BACKGROUND OF THE INVENTION

1 Field of the Invention Resistance to infectous disease is the result of both innate and acquired immunity. Innate immunity is nonspecific and involves the body's defense mechanisms such as a the skin barrier, secretions, and the cough reflex, whereas acquired immunity is very specific and often involves the production of a specific response (antibody) to a specific stimulus (antigen) which may be a foreign substance or a natural substance which has gone awry.

The complement system serves as one part of the immune system and is also activated both by specific substances (antibody) and by the nonspecific substances (e.g. yeast wall and pneumococcal cell wall). The complement response involves a series of biochemical reactions in which one protein acts on another, which in turn acts on another and so on. These proteins are designated by a alphabetical abbreviations and numbers commonly accepted in the field of immunology (e.g. Cl, B, P). Ultimately, this cascade may lead to the entrapment and/or cytolosis (destruction) of the offending substance. There are a number of other mechanisms by which the body defends itself, but for the purposes of brevity and simplicity, these have been omitted here.

As with any body function, the immune response does not always work perfectly or in the best interests of the individual. Allergies, for example, are the result of an overzealous immune response and are often quite harmful to the individual. Organ transplant rejection, on the other hand, is an example of an appropriate immune response which is detrimental to the individual. Similarly, there are a whole variety of autoimmune diseases which result from the immune response attacking the individual's own cells.

These immune and autoimmune disease represent a class of disease which are often difficult to treat effectively. lthough there are a number of drugs which exist to treat them, none are adequate to control or inhibit complement activation. The inhibition of complement may be very important in a variety of these diseases because as the complement system becomes active, there may be destruction and removal of cells and substances, which is detrimental to the individual. It is useful, therefore, to have substances which can be administered to patients to prevent active complement activation.

Diseases in which such a substance may be therapeutically useful include paroxysmal nocturnal hemoglobulinurea, rheumatoid arthritis, (in which the substance might be administered directly to a joint capsule to prevent complement activation), and hereditary angi-oedema, (in which deficiency of a complement control protein leads to very active complement consumption).

Heparin, a polydisperse sulfated polysaccharide, is used primarily as a blood anticoagulant during many medical and surgical procedures. Although this is heparin's primary activity, it also displays other secondary activities such as its ability to inhibit complement activity. However, heparin's potency as an anticoagulant has made its use as a complement activation inhibitor problematic. The use of anticoagulant active heparin for the treatment of immune related disorders can result in hemorrhagic complications.

Heparin's anticoagulant activity has been demonstrated to be associated with the presence in its structure of a specific sequence for the binding of antithrombin III. Once bound to heparin, antithrombin III can then inhibit a number of blood coagulation factors, and thus prevent coagulation of blood. Several approaches have been used to separate heparin's anticoagulant (primary) activity from its complement cascade inhibition (secondary) activity. The removal of this antithrombin III binding sequence from heparin permits the exploitation of this drug for the treatment of immune related disorders Such disease states for which this drug would be useful include septic shock, rheumatoid arthritis, lupus and systemic lupus erythematous.

Heparin's anticomplement activity is mediated by binding to a variety of complement proteins and thereby regulates both the classical and alternate amplification pathways. Heparin inhibits a portion of the complement cascade by inhibiting generation of the cell bound amplification pathway C3 convertases, C3b,Bb, C3b,Bb,P and C3b,Bb,Nef. It also acts as a complement inhibitor by interfering with the binding site on C3b for B. Furthermore, it prevents the consumption of B by D in the presence of C3b again indicating a direct action on C3b.

2. Prior Art

Heparin has been used for the last half century as an anticoagulant. Commercial heparin, with an average molecular weight of 10,000–14,000, also possesses a multiplicity of other biological activities including an ability to regulate complement activation. The structure-activity relationship for heparin is well understood for anticoagulant activity, but is poorly understood with effect on the complement system. Moreover, heparin's anticomplement activity is heretofore been coupled with its anticoagulant activity which often is an undesirable side effect.

Therefore, it is desirable to provide isolated components of heparin which have high anticomplement activity with low anticoagulant activity.

SUMMARY OF THE INVENTION

Depolymerized heparin is fractionated to recover a mixture of polysaccharide fragments. Further fractionation on the basis of size permits the isolation of a tetrasaccharide mixture, a hexasaccharide mixture, an octasaccharide mixture, a decasaccharide mixture and a mixture comprised of higher oligosaccharides. The tetrasaccharide mixture can be further fractionated into over 12 individual tetrasaccharide components. The mixture of polysaccharide fragments and the size separated fractions are all capable of inhibiting complement activation while all show less than 33% of undigested native heparin's anticoagulant activity. An individual hexasulfated tetrasaccharide having no detectable anticoagulant activity is disclosed which exhibits significant ability to inhibit complement activation. Said polysaccharide fragments may be employed therapeutically to treat immune disorders involving activation of complement including autoimmune diseases.

BRIEF DESCRIPTION OF THE DRAWINGS

The accompanying figures and drawings are provided to demonstrate the results obtained in the specific examples illustrating the invention.

Note: The flow rate in FIGS. 2a, b, c and d is 1.5 ml/min, chart speed is 15 cm/hr, 0.2 a.u.f.s., with a linear sodium chloride gradient at pH of 3.5.

Figure 2:
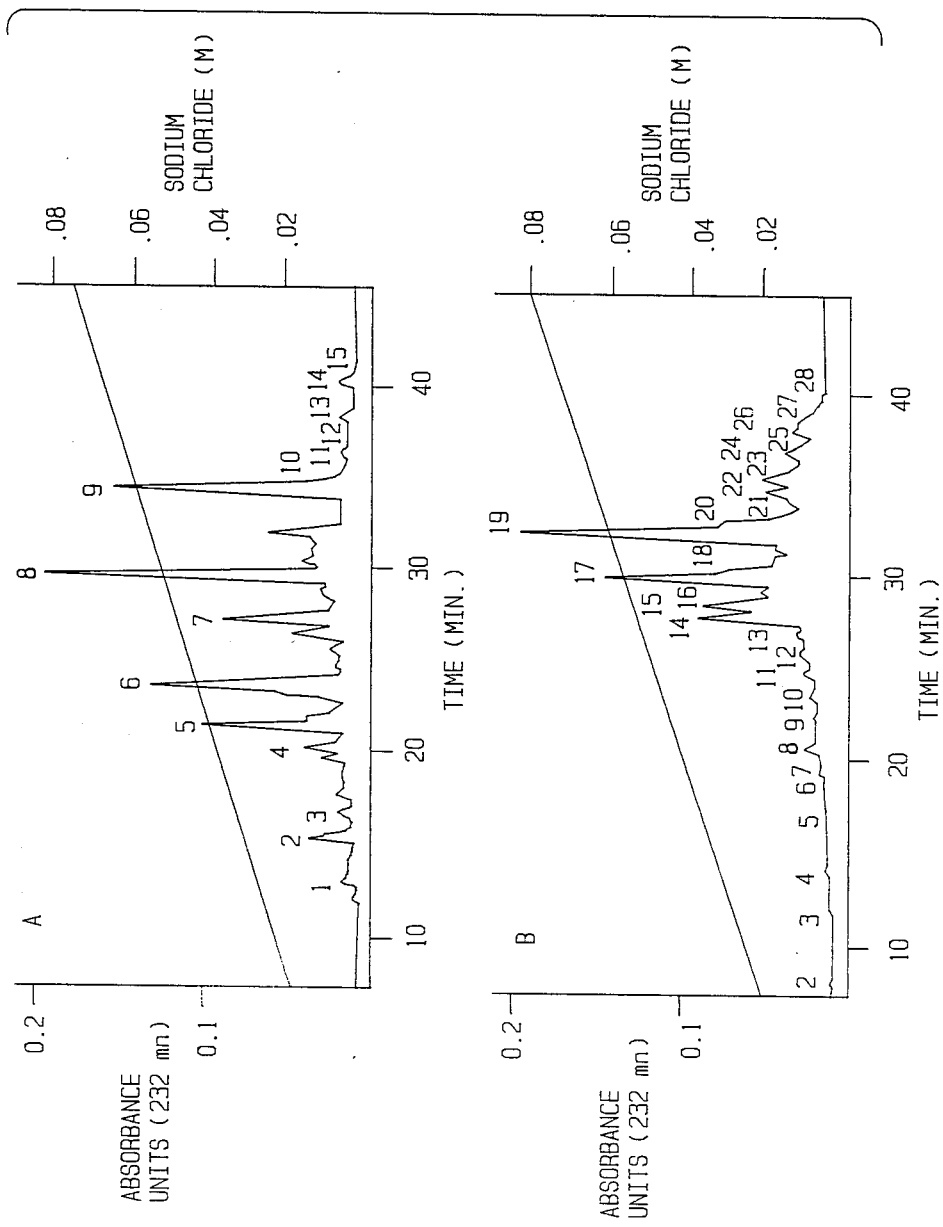
FIG. 2a represents the results of further separation utilizing high performance liquid chromatography of the heparin derived mixtures of tetrasaccharides.
FIG. 2b represents the results of further separation utilizing high performance liquid chromatography of the heparin derived mixtures of hexasaccharides.
FIG. 2c represents the results of further separation utilizing high performance liquid chromatography of the heparin derived mixtures of octasaccharides.
FIG. 2d represents the results of further separation utilizing high performance liquid chromatography of the heparin derived mixtures of decasaccharides.

FIG. 3a represents the results of an assay of the tetrasaccharide mixture eluted in FIG. 2a plotting the component number against the percent of native heparin's anticomplement activity.

FIG. 3b represents the results of an assay of the hexasaccharide mixture eluted in FIG. 2b plotting the component number against the percent of native heparin's anticomplement activity.

Figure 3C:
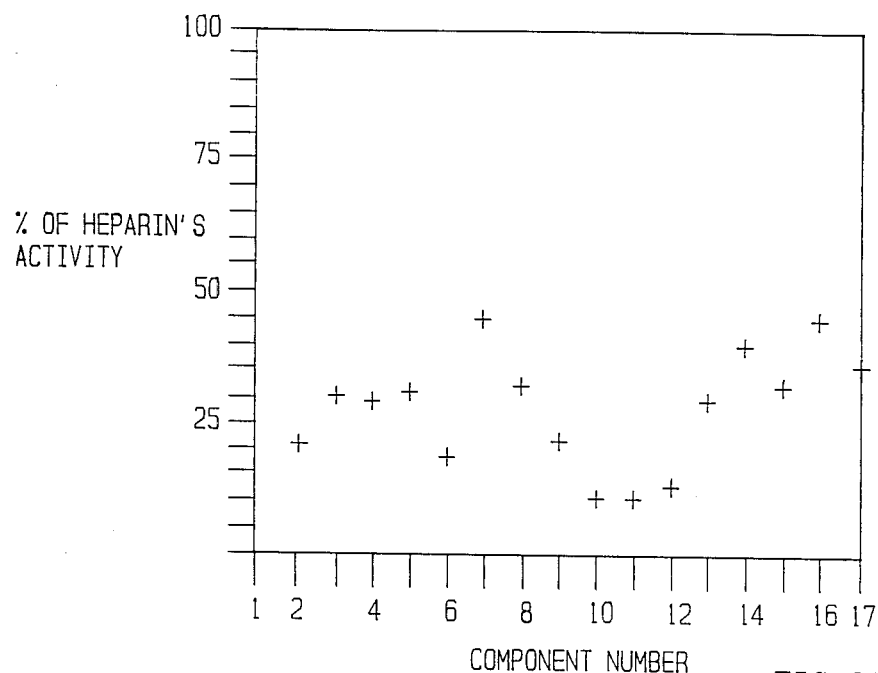

FIG. 3c represents the results of an assay of the octasaccharide mixture eluted in FIG. 2c plotting the component number against the percent of native heparin's anticomplement activity.

Figure 3D:
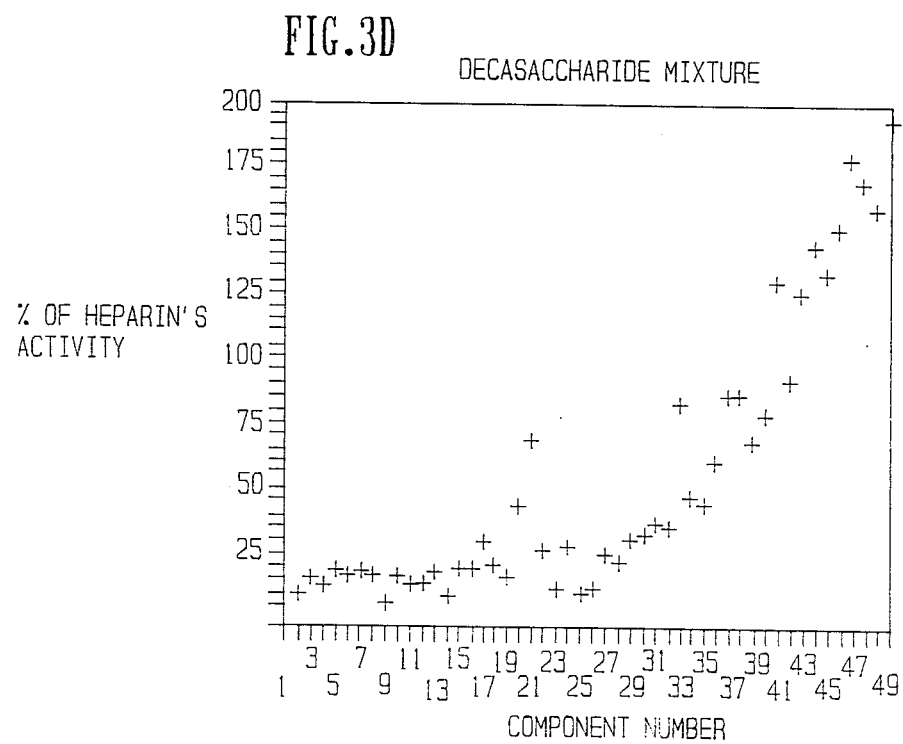

FIG. 3d represents the results of an assay of the decasaccharide mixture eluted in FIG. 2d plotting the component number against the percent of native heparin's anticomplement activity.

Figure 4:
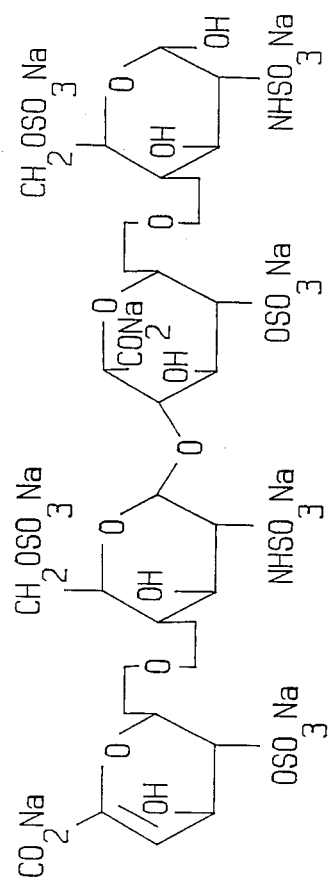

FIG. 4 is a representative of the structural for the hexasulphated tetrasaccharide characterized in Example III.

DESCRIPTION OF THE PREFERRED EMBODIMENTS

The compositions of this invention are characterized by the capacity to inhibit complement activation, while having little or no anticoagulant activity. The compositions of this invention are obtained by depolymerizing native heparin with heparinase. The mixture of polysaccharides obtained by the heparinase digestion have the desired anticomplement activity and have an average molecular weight of between 900 and 1200 and range from 500 to 5000.

Other methods of heparin depolymerization may be utilized including chemical hydrolysis, chemical eliminative cleavage, deaminative cleavage and oxidative cleavage.

Other compositions of this invention comprise fragments isolated from the above polysaccharide mixture. These fragments comprise:

a mixture of tetrasaccharides having an average molecular weight of 1,180 and a chain size of 4;

a mixture of hexasaccharides having an average molecular weight of 1,400 and a chain size of 6;

a mixture of octasaccharides having an average molecular weight of 2,300 and a chain size of 8;

a mixture of decasaccharides having an average molecular weight of 2,700 and a chain size of 10; and a mixture of higher oligosaccharides having an average molecular weight of 4,000 and a chain length of >10.

After heparin has been depolymerized using either a free or immobilized heparinase, the enzyme is removed by filtration, precipitation, chromatography or some other standard technique known to the art. The recovered polysaccharide mixture is then concentrated by freeze-drying or precipitation. The fragments thus obtain are redissolved in a suitable aqueous solution such as 1M ammonium bicarbonate and applied to a gel column at a high concentration, usually at 100 mg/ml. The column is packed with conventional chromatography gel beads of controlled pore size, such as Fractogel TSK 40 or 50, and then are eluted with a suitable aqueous solution such as 1 M ammonium bicarbonate.

The column effects separation of the fragments on the basis of size. Appropriate heparin and chondroitin derived carbohydrates of various well defined molecular weights are used as molecular weight standards. Further fractionation of the sized fragment mixtures is accomplished on the basis of charge using an anion exchanger, such as by high performance liquid chromatography on a column packed with strong anion exchanger. Such fractionation of the tetrasaccharide mixture resulted in the isolation of a hexasulfated tetrasaccharide (FIG. 4) having the appropriate anticomplement activity.

Similar fractionation has been accomplished on the other sized mixtures of fragmets and in each case, individual components have been isolated with the appropriate anticomplement activity. In all cases these individual components, with high activity to inhibit complement activation, have a degree of sulfation higher than the average for the polysaccharide mixture as a whole.

The sized mixtures of fragments are also fractionated using affinity chromatography. Columns packed with Antithrombin III-Sepharose are used to remove residual traces of anticoagulant activity from the sized fragment mixtures. Alternatively, complement proteins coupled to Sepharose are used to enrich the sized fragment mixtures in their ability to inhibit complement activation.

The sized fragment mixtures, as sodium salts, are characterized with respect to molecular weight by gel chromatography against standards of known molecular weight. Additionally their average molecular weight is estimated from their absorbance at a fixed concentration using the known molar absorptivity for their chromaphore. The structure of the hexasulfated tetrasaccharide (FIG. 4) was established by both proton and carbon nuclear magnetic resonance spectroscopy.

The degree of sulfation of individual components is established electrophoretically or chemically using a rhodizonate sulfate assay. The anticoagulant activity or absence thereof is determined using activated partial thromboplastin time and Factor Xa clotting assays as well as Thrombin-Antithrombin III and Factor Xa-Antithrombin III amidolytic assays. The capacity to inhibit complement activation is measured by the generation of the alternative pathway convertase, EAC4b,3b,Bb,P. The results of this activity assay is given in TABLE 1 and FIGS. 3a, b, c and d.

As noted above, the compounds of this invention can be isolated in the form of their sodium or ammonium salt. However, it is to be understood that the compounds of this invention can be utilized in the form of the free acids, other metallic or non-metallic salts.

Representative suitable salts include alkaline earth metal bases, ammonium and alkyl substituted ammonium salts or the like. These salts can be formed by any conventional means.

TABLE 1

| SAMPLE | CONCENTRATION (μgm) GIVING 50% INHIBITION OF EAC4b, 3b, Bb, P CONVERTASE |
|---|---|
| HEPARIN* | 7 |
| POLYSACCHARIDE MIXTURE | 75 |
| TETRASACCHARIDE MIXTURE | 85 |
| HEXASACCHARIDE MIXTURE | 75 |
| OCTASACCHARIDE MIXTURE | 36 |
| DECASACCHARIDE MIXTURE | 15 |
| LARGE OLIGOSACCHARIDE MIXTURE | 5 |
| HEXASULFATED TETRASACCHARIDE* | 90 |

*Heparin anticoagulant activity was 150 U/mg while the hexasulfated tetrasaccharide was <1 U/mg by all assays.

The following examples illustrate the present invention and are not meant to limit the same.

EXAMPLE I

Enzymatic Depolymerization of Heparin

Heparin fragments were prepared in a mixture of porcine mucosal heparin (50 mg/ml) and purified heparinase (heparin lyase EC-4.2.2.7) derived from *Flavobacterium heparinum* (5U/mg., 1 U=1 μmol bonds cleaved/min.) both, in buffer consisting of 0.25 M sodium acetate and 0.0025 M calcium acetate at pH 7. This mixture was shaken at 30° C. until the reaction reached completion. The pH of the mixture was then adjusted to pH 4 and the enzyme was removed by passage over a column containing SP-Sephadex C-50. The eluent containing the polysaccharide mixture was adjusted to pH 7 and freeze dried.

EXAMPLE II

Fractionation of Polysaccharide Compounds

Figure 1:
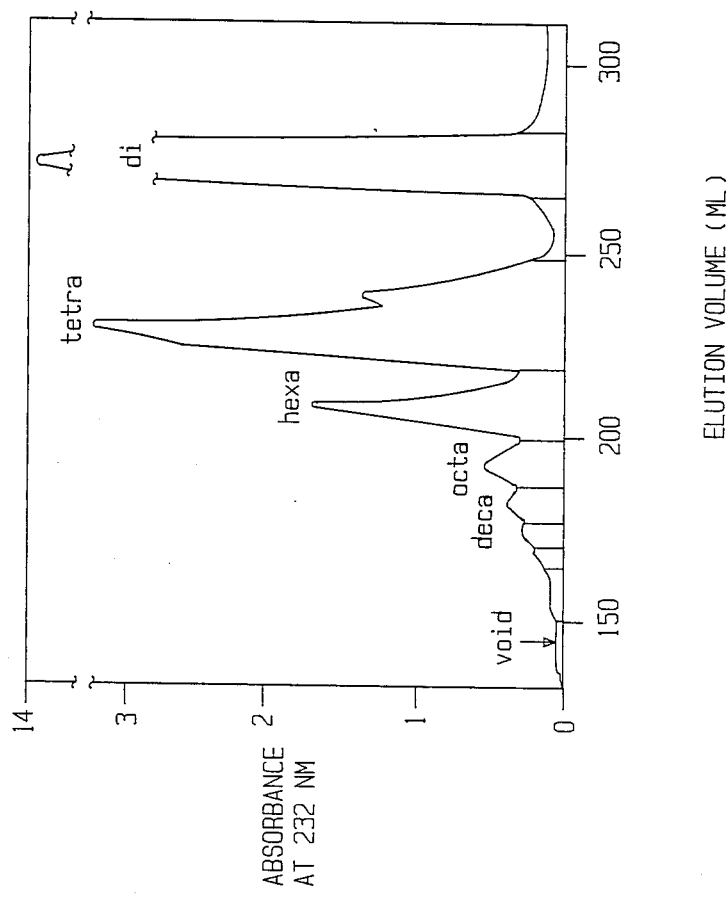
FIG. 1 represents fractionation of mixed depolymerized heparin fragments utilizing low pressure gel permeation chromatography.

The polysaccharide mixture obtained, as described in EXAMPLE I, was dissolved in water (500 mg in 2 ml) and was loaded onto a column packed with Fractogel TSK F40 (80×2.5 cm) and eluted with 1 M ammonium bicarbonate buffer at 0.3 ml/min. The eluent was diluted with water and its absorbance was measured at 232 nm (FIG. 1). Six distinct peaks were observed representing, from last to first eluted, disaccharide, mixed tetrasaccharide fragments, mixed hexasaccharide fragments, mixed octasaccharide fragments, mixed decasaccharide fragments and mixed higher oligosaccharide fragments. These peaks were identified on the basis of elution volume as compared to heparin and chondroitin derived standards of known molecular weight and by their absorbence at 232 nm based on a reported molar absorptivity of $5.2 \times 10^3 M^{-1}$.

Each sized fragment mixture (1 mg in 0.01 ml) was then applied to a strong anion exchange high performance liquid chromatography column and eluted using 180 ml linear gradient ($Y + 1.5 \times 10^{-4}$ M/sec × +0.2 M, sodium chloride at pH 3.5) and detected by absorbence at 232 nm (FIG. 2a-d). The resulting individual components were collected, dialyzed against 1000 volumes of water using controlled pore dialysis membranes (MW cutoff =1,000) and freeze dried.

Further fractionation of either the polysaccharide sized mixture or the individual components separated by affinity chromatography involved the use of either immobilized antithrombin III or an immobilized complement protein such as C3b. These proteins were immobilized onto cyanogen bromide activated Sepharose by standard methods. The immobilized protein was then packed into a column equilibrated with 50 mM phosphate buffer (pH 7) and the fragment sample in the same buffer was applied. When using antithrombin III as the affinity matrix, the eluent was collected, dialyzed (as above), freeze dried and was then measured for biological activity When using immobilized complement proteins, such as C3b as the affinity matrix, the eluent initially obtained in 50 mM buffer was discarded and the column was washed first with 5 column volumes of 50 mM buffer and then with 1 column volume of 2 M phosphate buffer (pH 7) to elute the fragments which initially bound to the column. These fragments were then dialyzed (as above), freeze dried and measured for biological activity.

EXAMPLE III

Structural Elucidation

The structure of the hexasulfated tetrasaccharide (FIG. 4), as well as the other individual fragment components was determined by using chemical, electrophoretic and spectroscopic methods. The degree of sulfation was determined using either: (1) the rhodizonate assay for inorganic sulfate after pyrolysis of the sample, or (2) by paper electrophoresis of the unmodified fragment. The number of uronic acid residues was measured using carbazole dye reagent. The precise structure of the hexasulfated tetrasaccharide was established using (90.6 MHz) $^{13}C$ and (360 MHz) $^1H$ nuclear magnetic resonance spectroscopy at 0.05 M in D$_2$O.

EXAMPLE IV

Biological Assay

The ability of a fragment or mixture of fragments, at concentrations from 1-50 μgm, to inhibit complement activation was determined by hemolytic assay. Half-isotonic veronal-buffered saline, pH 7.5 containing 0.1% gelatin (GVB), GVB containing 2.5% dextrose, 0.5 mM magnesium and 0.15 mM calcium (DGVB++) and GVB containing 40 mM EDTA were used as buffers in the hemolytic assays.

Complement proteins C3 (Tack and Prahl, Biochemistry 15:4513), B (Hunsicker et al., J. Immunol 110:128), D (Fearon and Austen, J. Exp. Med 142:856) and P (Fearon and Austen, Proc. Natl. Acad. Sci. USA. 74:1683) were purified to homogeneity and quantitated as described. C3b was generated from purified C3 as described previously (Gitlin et al., J. Exp. Med. 141:1221; Weiler et al., J. Exp. Med 147:509). Rat serum, as a source of terminal components, was obtained from Rockland Inc. (Gilbertsville, Pa.).

EAC4b,3b cellular intermediates were prepared as described previously (Fearon et al., J. Exp. Med. 138, 1305; Lachmann and Hobart, Handbook of Experimental Immunology, 3rd Edn. Chapter 5a). Heparin and its fragments were examined for ability to inhibit generation of the amplification pathway convertase as previously described (Weiler et al., J. Exp. Med 147:509): 100 μl of DGVB++ alone or DGVB++ containing a heparin or heparin fragment dilution was added to tubes (Falcon 2052, Becton-Dickinson, Oxnard, CA). At time zero, 100 μl of DGVB++ containing a suspension of $1 \times 10^7$ EAC4b,3b, 0.28 ng B, 100 ng P and 10 ng D, was added to each tube. The tubes used for the reagent blank and for 100% lysis contained no B. The mixtures were incubated for 30 min at 30° C. with shaking. Then 0.3 ml of 1:15 dilution of rat serum in 40 mM EDTA was added to each tube and incubation continued for 60 min at 37° C. Saline (1.5 ml) was then added to each tube except that the 100% tube was lysed with 1.5 ml of water in place of the saline. Finally, the contents of the tubes were mixed well, centrifuged and percent lysis and the average number of hemolytic sites was determined.

The results of this assay for the sized fragment mixtures and the hexasulfated tetrasaccharide are given in TABLE 1. The results of this assay for the individual fragments of tetra-, hexa-, octa-, and deca-saccharide size are given in FIG. 3a, b, c and d. These figures are plots of wt. % heparin's complement inhibition activity vs. peak number eluting from the ion-exchange column (FIG. 2a, b, c and d). The anticoagulant activity of 1-50 μgm of a fragment or mixture of fragments was assessed by activated partial thromboplastin time and factor Xa coagulation assays and by thrombinantithrombin III and factor Xa-antithrombin III amidolytic assays.

We claim:

1. A compound derived from depolymerized heparin comprising a free acid or metallic or non-metallic salt of a tetrasaccharide, a hexasaccharide, an octasaccharide, or a mixture thereof, wherein said compound has biological activity to inhibit complement activation, wherein said compound has diminished anticoagulant activity as compared to native heparin, and wherein the molecular weight of said compound is no greater than about 2300 daltons.

2. The compound of claim 1 wherein said compound is obtained by heparinase EC-4.2.2.7 digestion.

3. The compound of claim 1 wherein the compound is a tetrasaccharide.

4. The compound of claim 3 wherein the tetrasaccharide is a hexasulfated tetrasaccharide.

5. The compound of claim 1 wherein the compound is a hexasaccharide.

6. The compound of claim 1 wherein the compound is an octasaccharide.

7. A compound derived from depolymerized heparin, comprising a free acid or metallic or non-metallic salt of a decasaccharide, said compound has biological activity to inhibit complement activation and has diminished anticoagulant activity as compared to native heparin.

8. A method of treating immune disorders in mammals, comprising the intravenous administration of the decasaccharide of claim 7.

* * * * *